US007754472B2

(12) United States Patent
Schwind et al.

(10) Patent No.: US 7,754,472 B2
(45) Date of Patent: Jul. 13, 2010

(54) DEVICE AND METHOD FOR DETECTING ANALYTES BY VISUALIZATION AND SEPARATION OF AGGLUTINATION

(75) Inventors: Peter Schwind, Fribourg (CH); Philippe Monod, Posieux (CH)

(73) Assignee: Medion Diagnostics AG, Dudigen (CH)

( * ) Notice: Subject to any disclaimer, the term of this patent is extended or adjusted under 35 U.S.C. 154(b) by 283 days.

(21) Appl. No.: 10/587,964

(22) PCT Filed: Feb. 2, 2005

(86) PCT No.: PCT/EP2005/001029

§ 371 (c)(1),
(2), (4) Date: Feb. 19, 2009

(87) PCT Pub. No.: WO2005/090970

PCT Pub. Date: Sep. 29, 2005

(65) Prior Publication Data

US 2009/0170062 A1   Jul. 2, 2009

(30) Foreign Application Priority Data

Feb. 2, 2004   (DE) .................. 10 2004 005 193

(51) Int. Cl.
*G01N 33/53* (2006.01)
(52) U.S. Cl. .............. 435/283.1; 435/7.1; 435/7.94; 435/287.1; 435/288.2; 435/288.4; 435/297.4; 435/960; 436/514; 436/518; 436/523; 436/526; 436/535; 436/805
(58) Field of Classification Search ............... 435/7.1, 435/7.94, 283.1, 287.1, 288.2, 288.4, 297.4, 435/960; 436/514, 518, 523, 526, 535, 805; 422/58
See application file for complete search history.

(56) References Cited

U.S. PATENT DOCUMENTS 5,637,469 A * 6/1997 Wilding et al. .............. 435/7.21
5,866,345 A * 2/1999 Wilding et al. .............. 435/7.21

(Continued)

FOREIGN PATENT DOCUMENTS

CA   2 323 424   3/2005

(Continued)

*Primary Examiner*—Bao-Thuy L Nguyen
(74) *Attorney, Agent, or Firm*—RatnerPrestia

(57) ABSTRACT

The invention relates to a device for detecting one or several analytes in a sample, characterized in that it comprises one or more reaction chambers and/or one or more reagent application channels, and one or more capillary systems and one or more negative vessels. The invention also relates to a method for detecting one or more analytes in a sample fluid by visualization of agglutination, characterized in that a) the sample fluid is brought into contact with a reagent, b) the reaction mixture is exposed to the effects of gravitation or magnetism, wherein the reaction mixture is strained through the capillary system of the inventive device with a negative vessel connected to the inventive device, and c) the reaction between the analyte and the reagent is determined. The invention also relates to one such method wherein the reaction mixture is brought into contact with another reagent during step b). The invention further relates to a method wherein the order of the individual steps consisting of a) and b) are reversed, particularly when the sample fluid is brought into contact with a reagent only during the effects of gravitation or magnetism.

31 Claims, 7 Drawing Sheets

U.S. PATENT DOCUMENTS

| | | |
|---|---|---|
| 6,203,706 B1 | 3/2001 | Schwind et al. |
| 6,214,629 B1 * | 4/2001 | Freitag et al. ............... 436/518 |
| 6,551,841 B1 * | 4/2003 | Wilding et al. .............. 436/518 |
| 6,632,619 B1 * | 10/2003 | Harrison et al. .............. 435/7.2 |
| 6,900,021 B1 * | 5/2005 | Harrison et al. ............ 435/7.21 |
| 7,005,292 B2 * | 2/2006 | Wilding et al. ........... 435/287.1 |
| 7,381,571 B2 * | 6/2008 | Woudenberg et al. ....... 436/518 |
| 7,494,770 B2 * | 2/2009 | Wilding et al. ................. 435/6 |
| 7,569,398 B2 * | 8/2009 | Puget et al. ................. 436/518 |
| 2003/0129671 A1 | 7/2003 | Wilding et al. |
| 2005/0112782 A1 * | 5/2005 | Buechler .................... 436/518 |
| 2006/0003463 A1 * | 1/2006 | Gilton ........................ 436/518 |
| 2008/0241962 A1 * | 10/2008 | Wang ......................... 436/514 |

FOREIGN PATENT DOCUMENTS

| | | |
|---|---|---|
| EP | 0485228 A | 5/1992 |
| WO | WO 99/46045 | 9/1999 |

* cited by examiner a)

b)

1  2  3  4  5

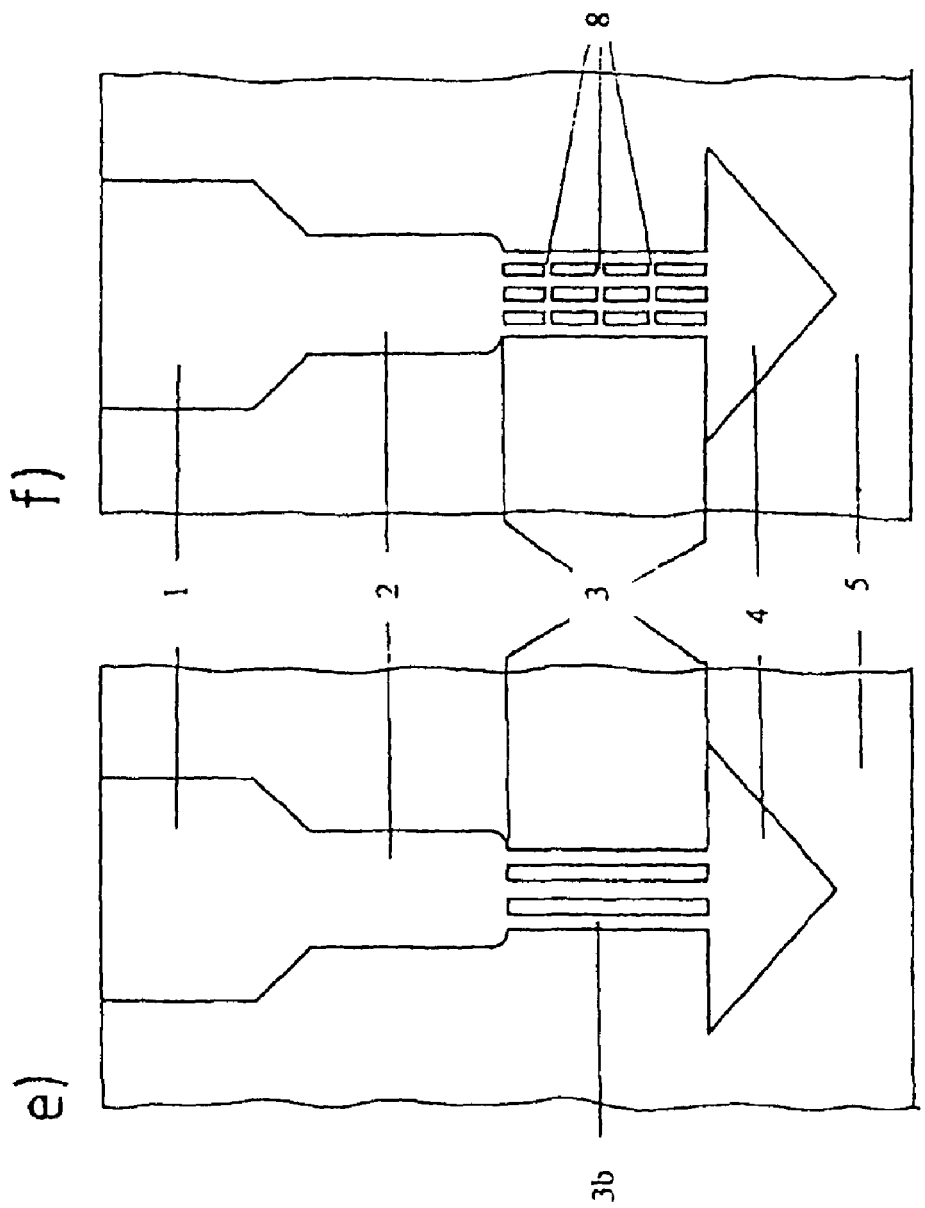

DEVICE AND METHOD FOR DETECTING ANALYTES BY VISUALIZATION AND SEPARATION OF AGGLUTINATION

CROSS-REFERENCE TO RELATED APPLICATIONS

This application is a U.S. National Phase Application of PCT International Application PCT/EP2005/01029, filed Feb. 2, 2005, incorporated herein by reference, which claims priority on German Patent Application DE 2004 10 005 193, filed Feb. 2, 2004.

FIELD OF THE INVENTION

The present invention relates to a device and method for detecting one or more analytes in a sample fluid by the visualization of agglutination reactions, in particular haemagglutination or particle agglutination reactions.

BACKGROUND OF THE INVENTION

Methods for detecting analytes by haemagglutination as well as particle agglutination tests are known. Methods are known for haemagglutination, wherein haemagglutinates are separated by a centrifuging step, through an inert matrix, from individual non-agglutinated erythrocytes (e.g. EP-A-0194212, EP-A-0305337, EP-A-0485228, EP-A-0725276). According to this method, agglutinated erythrocytes are retained on or in the inert matrix and can thus be separated from non-reacting individual erythrocytes, which may pass through the matrix and may deposit on the bottom of the reaction vessel.

The separation matrices are normally porous matrices (for example made of glass); gel bead matrices (for example of SEPHADEX®, SEPHACRYL®, AGAROSE®: EP-A-9184212, EP-A-0305337) or glass bead matrices (EP-A-0725276).

All these systems have in common that the separation matrix and the carrier element system comprise two separate components. The same applies to likewise disclosed methods, wherein, instead of beads, porous or filter matrices are used. The carrier element system is manufactured, as the case may be, by conventional (macro) injection molding methods.

The aforementioned matrices are used in blood group serological diagnostics, in particular for the visualization of haemagglutination reactions. They generally detect parameters, which are of importance in particular with regard to transfusions or the morbus haemolyticus neonatorum. In this context, this concerns inter alia the detection of antigens on the surface of those erythrocytes which are characteristic of the blood groups. Further important antigen systems are also to be found on thrombocytes, granulocytes, lymphocytes, which likewise play a role in transfusions and/or transplantations. Moreover, haemagglutinating viruses may be detected in a similar manner.

The aforementioned matrices, in particular gel bead matrices, are used for particle agglutination tests as well. However, to date only synthetic particles are used, meeting tight specifications, in particular having a high specific density and a lower diameter than erythrocytes (e.g. specific density $\geq/=1.1$; diameter $<5$ μm; cf. EP-0849595).

The prior art methods present a number of drawbacks. Although a spatial separation of haemagglutinated and individual erythrocytes is obtained by centrifuging, the reaction matrix for positive and negative reactions, however, comprises a single compartment, so that the passage from negative (non-agglutinated) to positive (agglutinated) reactions is fluid and the evaluation of the results is thus subject to a certain subjectivity. Particularly in the case of slightly positive reactions, the indistinct demarcation in relation to negative results may result in interpretation difficulties. Furthermore, the reproducibility of the known methods, functioning, in particular, with a gel bead matrix, depend considerably on the matrix quality, normally polyacrylamide. These gels differ from one charge to the other, resulting in detection reactions which differ considerably in intensity of detection in the same sample. This makes it more difficult to standardize and reproduce the results. The sensitivity of the gel particles in relation to any type of shear forces resulting, in particular, in broken gel particles, is a further problem, which may lead to distorted reaction results. In addition, all matrices mentioned here have in common that they are three-dimensional and that a large component of the matrix space consists of matrix polymers, resulting in part of the colored particles, enclosed in the matrix, remaining invisible to the naked eye, i.e. not being able to contribute to detection. Furthermore, these methods are little suited for detecting thrombocyte properties in intact thrombocytes, since thrombocytes do not pass very well through the gel.

SUMMARY OF THE INVENTION

It is, therefore, an object of the present invention to overcome the disadvantages cited with regard to the state of the art, in particular the indistinct separation of the detection of slightly positive reactions in relation to negative reactions in the known matrices and variations from charge to charge in gel matrices, without having to abandon the advantages of the methods according to the state of the art, such as, for example, the mechanical stability of the agglutinates retained in the matrix (stable end point). In particular, a separating matrix in the absence of gel particles is to be provided, i.e. a space without a matrix in the known, narrower sense is to be provided, wherein the regions for positive and negative reactions are spatially separated without fluid transition.

This object is attained according to the invention by a device for detecting one or more analytes in a sample, on the one hand, characterized in that it includes one or a plurality of reaction chamber(s) and/or one or a plurality of reagent application channel(s) and one or a plurality of capillary system(s) and one or a plurality of negative vessel(s).

BRIEF DESCRIPTION OF THE DRAWINGS

In the following the invention is elucidated in more detail by figures and examples in a non-limiting manner. There is shown in.

DETAILED DESCRIPTION OF THE INVENTION

Figure 1:
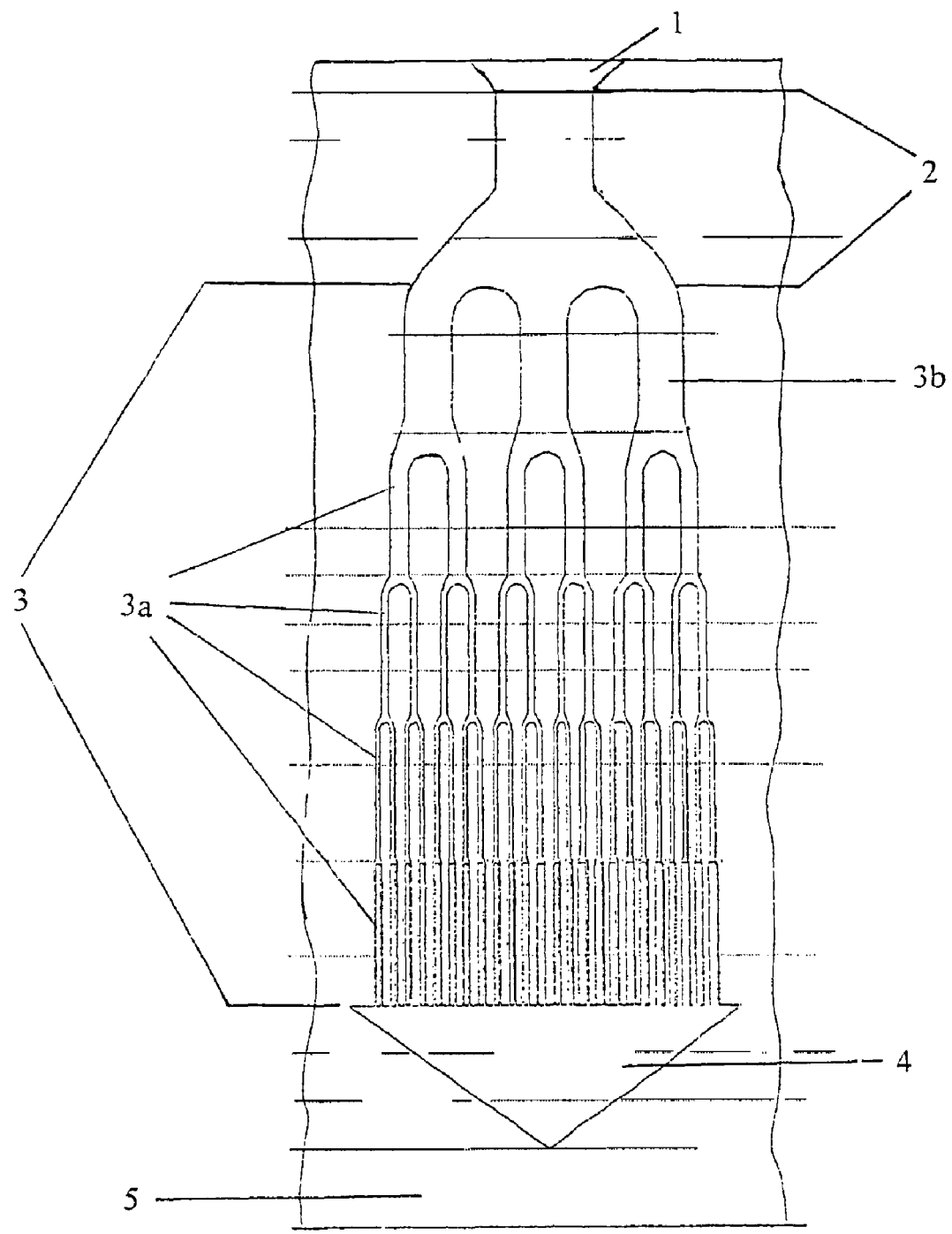
FIG. 1 an illustration of a device according to the invention including a plurality of capillaries disposed next to one another in a plurality of capillary planes, the diameters of the individual capillaries in the higher-lying planes being greater than those in the lower-lying planes.

The capillary system of the device according to the invention, preferably following on to a reaction chamber or a reagent application channel, forms an integral part of a carrier element, which is preferably made of synthetic materials, for example polyethylene, polypropylene, polystyrene, Topas or polymethyl methacrylate, and which is itself matrix-free.

A capillary system comprises at least one capillary of a capillary plane or one or a plurality of capillaries, which are branched or present a diminished cross-section in one or a plurality of capillary plane(s). In a preferred embodiment of the device it comprises one or a plurality of capillaries, which diminish, by degrees, in further capillary planes, which are in each case arranged one below the other and which, at the end, accumulate in a negative vessel. The capillary system includes at least one capillary of a plane terminating in a negative vessel. In one embodiment of the invention a plurality of capillaries are arranged next to one another or in bundles per capillary plane. Preferably, capillaries of a capillary plane disposed in adjoining or bundled formation have the same inner cross-sectional area for the fluid to be tested. The more distant the inner cross-sectional area of the capillary or capillaries of a capillary plane is disposed from the reaction chamber, the smaller it becomes.

One embodiment of the device according to the invention comprises a capillary system including only a single capillary of a capillary plane. By way of example, the inner cross-sectional area of a capillary is in this context less than 250.000 $\mu m^2$.

In a preferred embodiment, the capillary planes of the capillary system are connected by chambers, whose inner cross-sectional area is preferably the same as that of the capillary having the largest diameter, in which context the chambers serve preferably for ventilation or pressure balancing. In a further embodiment of the device according to the invention capillaries of a capillary plane arranged in an adjoining fashion comprise connecting webs by which they are interconnected.

In a preferred embodiment, the capillaries (provided there is more than one capillary) of the device according to the invention are disposed in each plane parallel side by side and not in bundled fashion, which makes it possible to use the color of the particles optimally for the detection.

The device according to the invention preferably includes a reagent application channel, In a particularly preferred embodiment of the device according to the invention the reagent application channel is pre-filled with a reagent, for example a buffer, booster solutions, antibodies. As an example, the reagent application channel has 1.2 times the volume as compared with the capillary system plus negative vessel.

In a preferred embodiment of the device according to the invention the negative vessel presents a shape, which constricts towards the bottom and becomes narrower, for example pointed downwardly like an arrow or U-shaped. At its upper side it is preferably at least as wide as the width of the sum of the capillaries of the lowermost capillary plane. The upper side of the negative vessel extends at a right angle or at any other angle, in particular smaller angle, to the capillary system. In one embodiment the negative vessel preferably has a larger volume than the volume of the compacted sediment of the cells or particles used. In a preferred embodiment the volume of the negative vessel is at least 0.8 times as large as the volume of the entire capillary system.

In a further preferred embodiment at least one ventilation channel is provided on the negative vessel, preferably at the widest part of a negative vessel, whose connection to the lower plane of the capillary system is preferably wider than the width of the sum of the capillaries of the lowermost capillary plane, preferably extending upwardly outside the capillary system.

In a particularly preferred embodiment a plurality of devices (reactors) according to the invention, each including at least one reaction chamber, and/or one reagent application channel and a capillary system and a negative vessel are combined parallel next to one another into a synthetic carrier element. Ventilation channels present there, by way of example, pass upwardly through the carrier element. In a further preferred embodiment partial regions of the exterior wall of a reactor, preferably in the region of the capillary system may be designed as an optical lens, conferring to the wall of an individual reactor or to the entire device according to the invention the function of a magnifying glass, in order to facilitate the reading of weak reactions.

A further subject of the invention is the use of the device according to the invention, in particular in blood group serological diagnostics, preferably for determining human and animal blood groups, antibodies against blood groups, for determining thrombocyte characteristics and antibodies directed against thrombocytes, for determining leucocyte characteristics and antibodies directed against leucocytes, for detecting haemagglutinating viruses, for detecting antibodies against peptides, proteins, carbohydrates, nucleic acids, viruses, bacteria, parasites, for detecting viral, bacterial and parasitic and other antigens and/or for detecting auto-antibodies and antibodies against allergens.

A further subject of the invention is a method for detecting one or more analytes in a sample fluid by the visualization of agglutination, characterized in that a) the sample fluid is brought into contact with a reagent, b) the reaction mixture is exposed to the effects of gravitation, in particular by centrifuging or magnetism, the reaction mixture passing through the capillary system of the device according to one of claims 1 to 13, followed by a negative vessel of the device according to one of claims 1 to 13 and c) the reaction between the analyte and the reagent is determined.

In a particular embodiment the reaction mixture is brought into contact with a further reagent during process step b).

In a further embodiment the order of the individual process steps consisting of a) and b) is reversed, in particular bringing the sample fluid into contact with a reagent is brought about only during the action of gravitation or magnetism. The sample fluid and/or the reagent preferably include one or more types of particles.

In the method according to the invention, in particular erythrocytes, thrombocytes and/or leucocytes or parts thereof are used as particles or, for example, a broad spectrum of synthetic particles of different materials and densities, preferably polystyrene particles, polybromostyrene-, magnetic and paramagnetic particles, melamine-, gelatine-, polymerized agarose, polymethyl methacrylate or other synthetic particles.

A positive reaction is characterized in that portions of the capillary system are visibly colored after centrifuging. The higher up the cells are retained, the more positive is the reaction. The reaction is preferably determined by the naked eye, by optical or electronic methods.

In particular embodiments the particles have a natural coloration or are colored or color-coded or radio-, fluorescent- and/or enzyme-coded. In a particular embodiment, particles are pre-treated with proteolytic enzymes in order to amplify the reaction.

Preferred reagents, for example for filling the reagent application channel, are, in particular, formulated solutions of monoclonal, polyclonal or recombinant antibodies or fragments thereof, which are directed against blood group characteristics, anti-human globulin antibodies or fragments thereof, alone or in combination with anti-human complement antibodies or fragments thereof and/or buffer solutions or booster solutions, containing no antibodies.

A further preferred reagent includes anti-human globulin antibodies or fragments thereof, alone or in combination with anti-human complement antibodies or fragments thereof, the density of the solution being increased, for example, by adding glycerin, a dextrane, a polyethylene glycol or other artificial or natural polymers. Increasing the density serves to create a barrier, which, under the centrifuging conditions, still allows erythrocytes to pass through while cell-free serum or plasma are kept back. In this manner it becomes possible to separate particle-bound IgG-molecules from non particle-bound IgG-molecules. The detection of particle-bound IgG-particles takes place, for example, by reacting with anti-human globulin reagents, which are preferably present in the condensed solution, and is made visible by agglutination. For this to be possible, the anti-human globulin reagent may not be neutralized in advance by unspecific IgG molecules present in the serum/plasma in excess. This procedure makes it possible to perform an indirect anti-human globulin test without a rinsing step.

A further subject of the invention is the use of the method according to the invention, in particular for determining blood groups, antibodies against blood groups, of compatibilities between stored blood units and recipients, for determining thrombocyte characteristics and antibodies directed against thrombocytes, for determining leucocyte characteristics and antibodies directed against leucocytes, for detecting haemagglutinating viruses, for detecting antibodies against viruses, bacteria, parasites, for detecting viral or other antigens or for detecting auto-antibodies or antibodies against allergens.

FIG. 1, by way of example, shows a device according to the invention including the feed end of a reaction chamber (1), a reagent application channel (2) of a capillary system (3), consisting of a plurality of capillary planes (3a) of diminishing cross-section, the diameters of the individual capillaries of the higher-lying planes being greater than those of the lower-lying planes, comprising a plurality of capillaries (3b), and a negative vessel (4), embedded in the carrier element (5).

Figure 2:
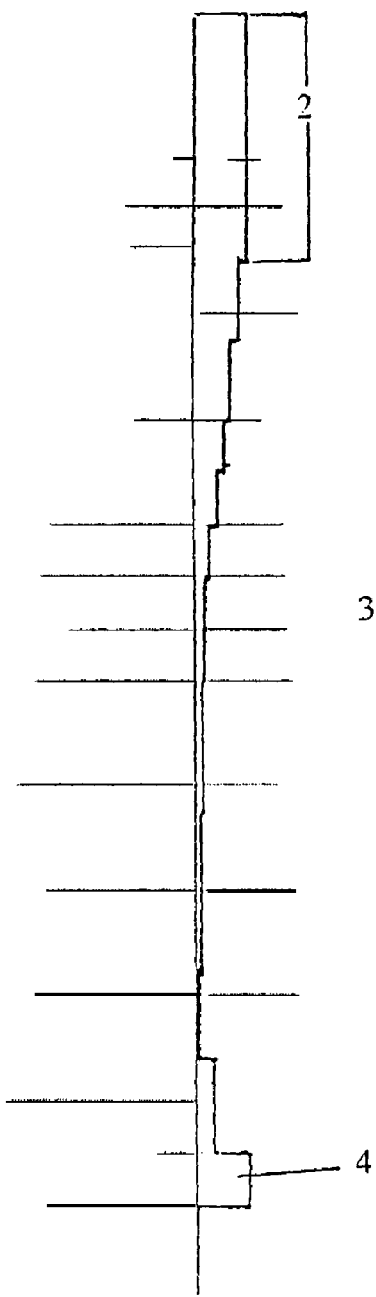
FIG. 2 an illustration of a side elevation of a device according to the invention including a plurality of capillary planes.

FIG. 2, by way of example, shows a side elevation of a device according to the invention including a reagent application channel (2) of a capillary system (3), consisting of a plurality of capillary planes (3a), the diameters of the individual capillaries of the higher-lying planes being greater than those of the lower-lying planes, comprising a plurality of capillaries (3b), and a negative vessel (4), embedded in the carrier element.

Figure 3:
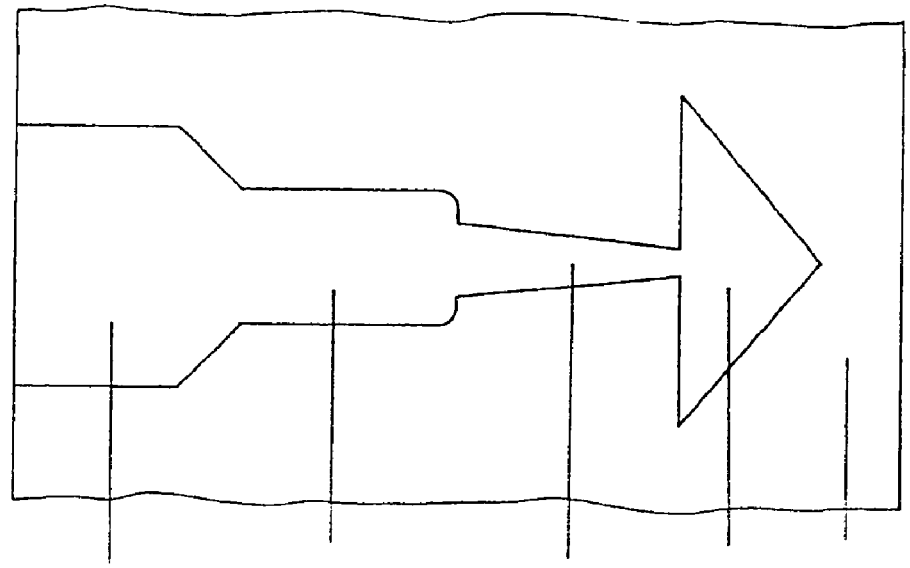
FIG. 3a an illustration of a device according to the invention comprising a capillary of a capillary plane.
FIG. 3b an illustration of a device according to the invention comprising a capillary of diminishing cross-section of a capillary plane.
FIG. 3c an illustration of a device according to the invention comprising three capillary planes with one capillary each.
FIG. 3d an illustration of a device according to the invention comprising three capillary planes with one capillary each, two chambers between interposed therebetween.
FIG. 3e an illustration of a device according to the invention comprising 3 capillaries of a capillary plane FIG. 3f an illustration of a device according to the invention comprising 4 capillaries of a capillary plane including connecting webs.
FIG. 3g an illustration of a device according to the invention comprising a capillary of a capillary plane including 2 ventilation channels leading out of the negative vessel.
Figure 3:
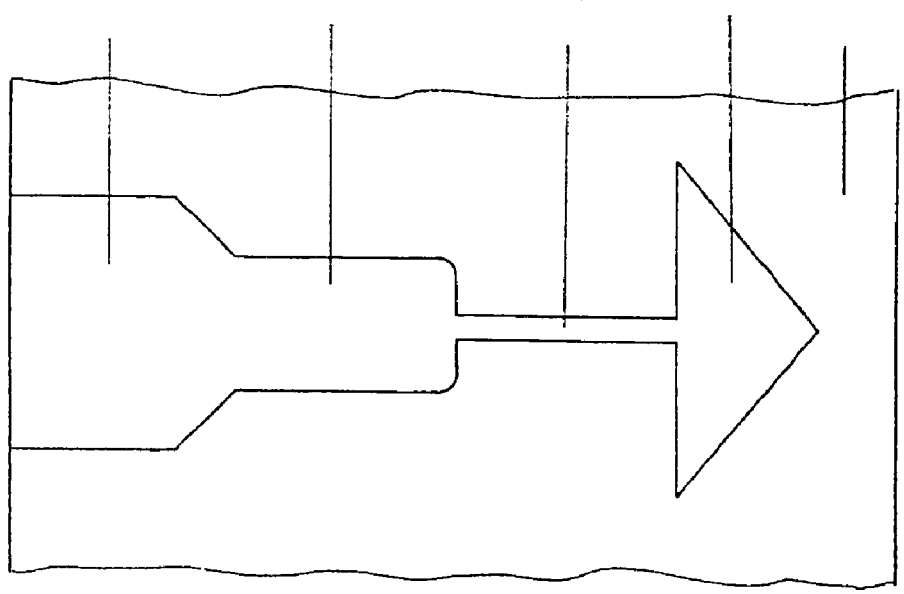
Figure 3:
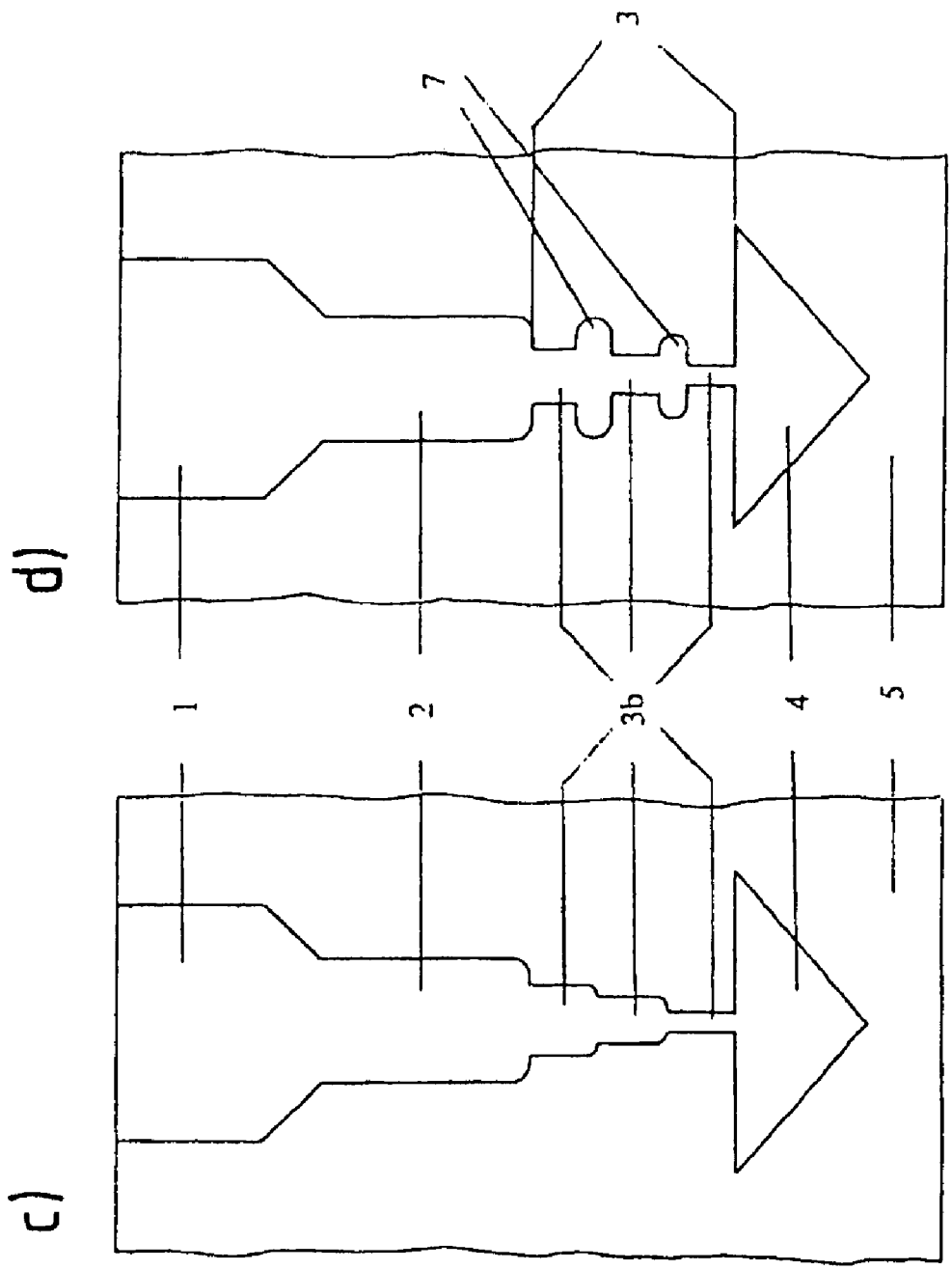
Figure 3:
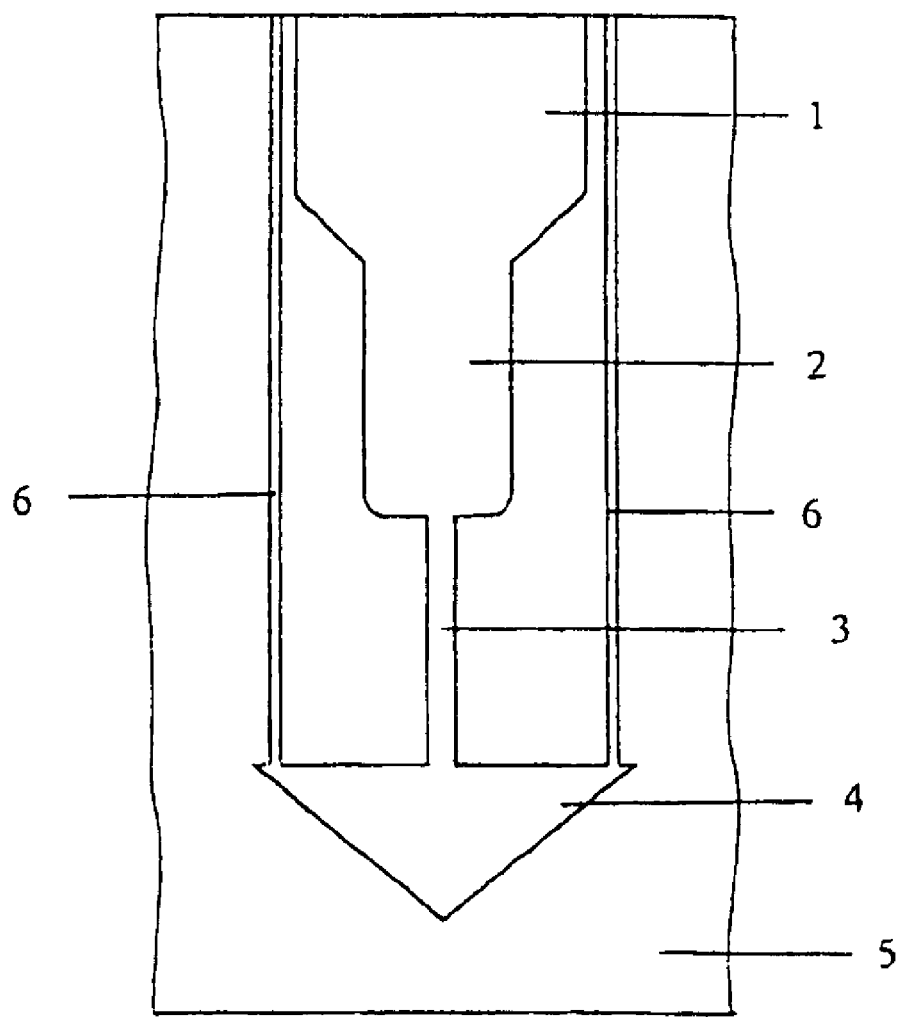

FIG. 3a, by way of example, shows a device according to the invention comprising a reaction chamber (1), a reagent application channel (2), a capillary system (3), consisting of a capillary of a capillary plane, and a negative vessel (4), embedded in the carrier element (5).

FIG. 3b, by way of example, shows a device according to the invention comprising a reaction chamber (1), a reagent application channel (2), a capillary system (3), consisting of a capillary of diminishing cross-section of a capillary plane, and a negative vessel (4), embedded in the carrier element (5).

FIG. 3c, by way of example, shows a device according to the invention comprising a reaction chamber (1), a reagent application channel (2), a capillary system (3), consisting of three capillary planes with one capillary each, and a negative vessel (4), embedded in the carrier element (5).

FIG. 3d, by way of example, shows a device according to the invention comprising a reaction chamber (1), a reagent application channel (2), a capillary system (3), consisting of three capillary planes with one capillary each, separated by chambers (7), and a negative vessel (4), embedded in the carrier element (5).

FIG. 3e, by way of example, shows a device according to the invention comprising a reaction chamber (1), a reagent application channel (2), a capillary system (3), consisting of three capillaries (3b) in a capillary plane (3a), and a negative vessel (4), embedded in the carrier element (5).

FIG. 3f, by way of example, shows a device according to the invention comprising a reaction chamber (1), a reagent application channel (2), a capillary system (3), consisting of four capillaries in a capillary plane, interconnected by connecting webs (8), and a negative vessel (4), embedded in the carrier element (5).

FIG. 3g, by way of example, shows a device according to the invention comprising a reaction chamber (1), a reagent application channel (2), a capillary system (3), consisting of a capillary of a capillary plane, and a negative vessel (4), from which two ventilation channels (6) at the upper edge are directed upwardly, embedded in the carrier element (5).

Figure 4:
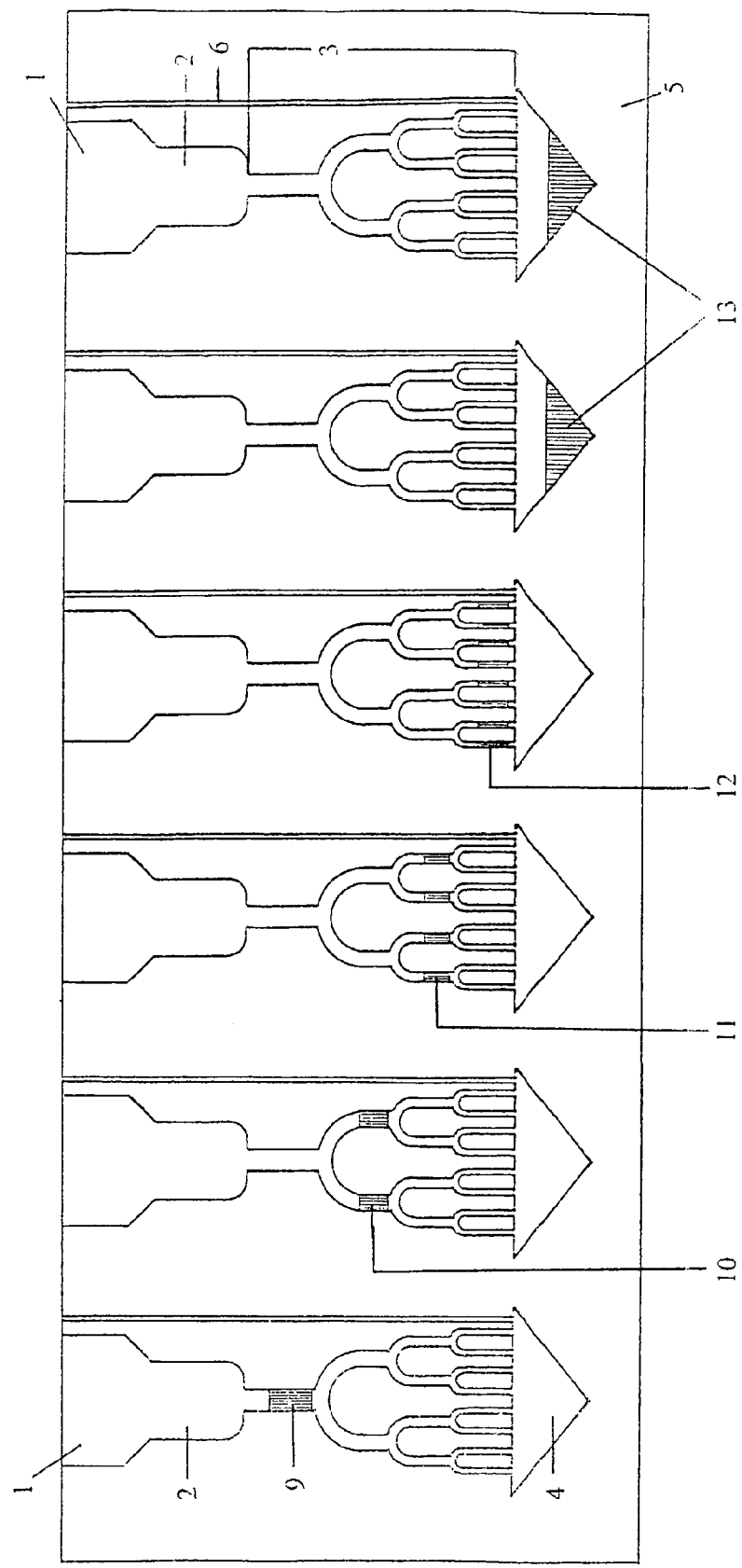
FIG. 4 an illustration of a plurality (six) of devices (reactors) according to the invention in a card, each comprising a ventilation channel and differently calibrated positive and negative results.

FIG. 4, by way of example, shows a card with six devices (reactors) according to the invention, each comprising a reaction chamber (1), a reagent application channel (2), a capillary system (3), consisting of a plurality of capillary planes with a plurality of capillaries, the diameters of the individual capillaries of the higher-lying planes being greater than those of the lower-lying planes, and a negative vessel (4), from which, at the upper edge, a ventilation channel (6) extends upwardly, embedded in the carrier element (5). The individual reactors of the card show differently calibrated positive results in the capillary system (3), namely a strongly positive reaction (9), a positive reaction (10), a weaker positive reaction (11) and a weakly positive reaction (12), and negative reactions (13) in the negative vessel (4).

EXAMPLES

1. Blood Group Determination
   a) Both reaction partners are pipetted into the reaction vessel.
      5 µl of a phosphate buffer are pipetted into a reagent application channel of a carrier element. It is centrifuged (10 min, 85 g) in an ID-centrifuge (Dia-Med).
      25 µl of a suspension of blood group A cells (ReverseCyte A1, Medion Diagnostics), diluted to 0.8%, are pipetted into the reaction chamber, followed by 5 μl of anti-A (BIRMA-1, Serologicals). The card is again centrifuged in the ID-centrifuge. Result: the haemagglutinates are retained in the capillary system. The negative vessel remains cell-free. If ReverseCyte B cells are used instead of ReverseCyte A1 cells, the cells collect visibly in the lower region of the negative vessel after centrifuging.

b) Pre-pipetted agglutination reagents
  5 μl anti-A (BIRMA-1, Serologicals) are pipetted into a reagent application channel of a carrier element. The card is centrifuged in an ID-centrifuge (10 min, 85 g). 25 μl of a suspension of blood group A cells (ReverseCyte A1, Medion Diagnostics), diluted to 0.8%, are pipetted into the reaction chamber. The card is again centrifuged in the ID-centrifuge. Result: the haemagglutinates are retained in the capillary system. The negative vessel remains cell-free. If ReverseCyte B cells are used instead of ReverseCyte A1 cells, the cells collect visibly in the lower region of the negative vessel after centrifuging.

c) Pre-pipetted agglutination reagent, full blood diluted in bromelin reagent
  5 μl anti-A (BIRMA-1, Serologicals) are pipetted into a reagent application channel of a carrier element. The card is centrifuged in an ID-centrifuge (10 min, 85 g). 50 μl of a suspension of anti-coagulated full blood of a person with blood group A are mixed with 500 μl of a bromelin reagent (Diluent 1, DiaMed) and left at room temperature for 10 minutes. Thereafter 10 μl of this suspension are pipetted into the reaction chamber. The card is immediately centrifuged in the ID-centrifuge. Result: the haemagglutinates are retained in the capillary system. The negative vessel remains cell-free. If instead of blood group A cells, blood group B cells are used, the cells collect visibly in the lower region of the negative vessel after centrifuging.

d) Agglutination reagent, pre-pipetted, but not pre-centrifuged, full blood diluted in bromelin reagent
  5 μl anti-A (BIRMA-1, Serologicals) are pipetted into a reagent application channel of a carrier element. 50 μl of a suspension of anti-coagulated full blood of a person having blood group A are mixed with 500 μl of a bromelin reagent (Diluent 1, DiaMed) and are left at room temperature for 10 minutes. Thereafter 10 μl of this suspension are pipetted into the reaction chamber. The card is immediately centrifuged in the ID-centrifuge. Result: the haemagglutinates are retained in the capillary system. The negative vessel remains cell-free. If instead of blood group A cells, blood group B cells are used, the cells collect visibly in the lower region of the negative vessel after centrifuging.

e) Determination of weak blood group characteristics in anti-human globulin test: Dweak
  5 μl anti-lgG in PBS, pH 7.4, 10% glycerin are pipetted into a reagent application channel of a carrier element. The card is centrifuged in an ID-centrifuge (10 min, 85 g). 50 μl of a suspension of anti-coagulated full blood of a person having blood group D, which presents weakly (Dweak), are mixed with 500 μl of a diluting solution (Diluent 2, DiaMed). From this suspension 25 μl are pipetted into the reaction chamber, followed by 25 μl of a commercial IgG anti-D product (ESD-1, DiaMed). Incubation takes places for 15 minutes at 37° C. and centrifugation in the ID-centrifuge. Result: The erythrocytes are haemagglutinated and the haemagglutinates are retained in the capillary system. The negative vessel remains cell-free. If instead of the blood group D positive cells, blood group D negative cells are used, the cells collect visibly in the lower region of the negative vessel after centrifuging.

2. Serum Counter-Test
  5 μl of a low-ionic buffer (DiaMed, Diluent 2) are pipetted into the reagent application channels of a carrier element. Thereafter 10 μl of a suspension of A1, A2, B, O-test cells each (DiaMed, ID-DiaCell AB0) are pipetted into 4 different reaction chambers of the carrier element, whereafter 10 μl of the plasma of a person to be tested having blood group A are also pipetted into this reaction chamber and the mixture is incubated for 10 minutes at room temperature (18 to 25° C.). The card is centrifuged in the ID-centrifuge. Result: The B cells react positively, the haemagglutinates are retained in the capillary system. The negative vessel of this reactor remains cell-free. The other three cells (A1, A2, O), which do not react with the isoagglutinines in the plasma used, collect visibly in the lower region of the negative vessel after centrifuging.

3. Antibody-Test
  a) Indirect anti-human globulin test (indirect Coombs test)
    5 μl of a mixture of anti-lgG and anti-C3d (Medion Diagnostics), condensed with 10% glycerin (w/v), are pipetted into a reagent application channel of a carrier element. The card is centrifuged in an ID-centrifuge (10 min, 85 g). 25 μl of a blood group O test cell for the antibody-search test (ScreenCyte 0.8% I, II, III, Medion Diagnostics) are pipetted into the reaction chamber, followed by 25 μl of patient serum. Incubation takes place for 15 minutes at 37° C. and centrifugation in the ID-centrifuge. Result: If the patient serum contains an irregular antibody, directed against an antigen present on one of the cells, the erythrocytes of the corresponding test cells are haemagglutinated and the haemagglutinates are retained in the capillary system. If the patient serum does not contain an irregular antibody, directed against an antigen present on one of the cells, the erythrocytes are not haemagglutinated. They collect as a visible red "button" in the lower region of the negative vessel after centrifuging.

b) Enzyme Test
    i) One-Phase Test
      5 μl of a phosphate buffer, pH 7.4, are pipetted into the reagent application channels of a carrier element. The card is centrifuged in an ID-centrifuge (10 min, 85). 25 μl of a blood group O test cell for the antibody search test (Screencyte I, II, III) are pipetted into the reaction chamber, followed by 25 μl of an enzyme reagent (Diluent 1, DiaMed) and 25 μl of patient serum. Incubation takes place for 15 minutes at 37° C. and centrifugation in the ID-centrifuge. Result: If the patient serum contains an irregular antibody, directed against an antigen present on one of the cells, the erythrocytes of the corresponding test cells are haemagglutinated and the haemagglutinates retained in the capillary system. If the patient serum contains no irregular antibody directed against an antigen present on one of the cells, the erythrocytes are not haemagglutinated. They collect as a visible red "button" in the lower region of the negative vessel after centrifuging.

ii) Two-Phase Test

5 µl of a phosphate buffer, pH 7.4, are pipetted into the reagent application channels of a carrier element. The card is centrifuged in an ID-centrifuge (10 min, 85 g). 25 µl of a papainised blood group O test cell for the antibody search test (ID-DiaCell IP, IIP, IIIP, DiaMed) are pipetted into the reaction chamber, followed by 25 µl patient serum. Incubation takes place for 15 minutes at 37° C. and centrifugation in the ID-centrifuge. Result: If the patient serum contains an irregular antibody, directed against an antigen present on one of the cells, the erythrocytes of the corresponding test cells are haemagglutinated and the haemagglutinates retained in the capillary system. If the patient serum contains no irregular antibody directed against an antigen present on one of the cells, the erythrocytes are not haemagglutinated. They collect as a visible red "button" in the lower region of the negative vessel after centrifuging.

c) Compatibility Test (Cross-Check)

5 µl of a mixture of anti-IgG and anti-C3d (Medion Diagnostics), density increased with 10% glycerin (w/v), are pipetted into a reagent application channel of a carrier element. The card is centrifuged in an ID-centrifuge (10 min, 85 g). The blood of a stored blood unit is diluted by mixing 10 µl cell sediment with 1 mL of a diluting solution (Diluent 2, DiaMed). Thereafter 25 µl of the diluted stored blood are pipetted into the reaction chamber, followed by 25 µl patient serum. Incubation takes place for 15 minutes at 37° C. and centrifugation in the ID-centrifuge. Result: If the patient serum contains an antibody, directed against an antigen of the erythrocytes of the stored blood, the latter are haemagglutinated and the haemagglutinates retained in the capillary system (donor and recipient incompatible). If the patient serum contains no incompatible antibody, the erythrocytes collect as a visible red "button" in the lower region of the negative vessel after centrifuging.

4. Direct Anti-Human Globulin Test (Direct Coombs-Test)

5 µl of a mixture of anti-IgG and anti-C3d (Medion Diagnostics), which has been condensed by 10% glycerin (w/v), are pipetted into a reagent application channel of a carrier element. The card is centrifuged in an ID-centrifuge (10 min, 85 g). 10 µl of an IgG charged Coombs-control cell (Coombs Control, Medion Diagnostics) are pipetted into the reaction chamber. Centrifugation takes place immediately in the ID-centrifuge. Result: Since the Coombs control cell is charged with IgG antibodies, the erythrocytes are haemagglutinated and the haemagglutinates retained in the capillary system. Non IgG-charged cells collect as a visible red "button" in the lower region of the negative vessel after centrifuging.

5. Particle-Agglutination with Centrifuging: Detection of Antibodies Against *T. pallidum*

5 µl of an anti-human IgG (Medion Diagnostics), which has been condensed by 10% g glycerin (w/v), are pipetted into a reagent application channel of a carrier element. The card is centrifuged in an ID-centrifuge (10 min, 85 g). A particle reagent (DiaMed, Syphilis polymer particles) coated with recombinant *T. pallidum* antigens (TpN15, TpN 17, TpN 47) is vortexed for 5 seconds at the highest setting. Thereafter 5 µl of a patient serum as well as 25 µl of the particle reagent are pipetted into the reaction chamber. After 5 minutes of incubation at room temperature, centrifugation takes place in the ID-centrifuge. Result: Patient serums containing antibodies against one or more of the syphilis antigens on the particles, agglutinate the particles so that they are retained in the capillary system similarly to the erythrocytes. Serums of non-infected persons do not agglutinate the particles. This causes the free particles to settle during centrifuging in the form of a visible brownish "button" in the lower region of the negative vessel.

6. Particle-Agglutination with Magnetic Separation: Detection of Antibodies Against *T. pallidum*

5 µl of an anti-human IgG (Medion Diagnostics), the density of which has been increased by 10% glycerin (w/v), are pipetted into a reagent application channel of a carrier element. The card is centrifuged in an ID-centrifuge (10 min, 85 g). Paramagnetic particles (estapor microspheres, France) coated with recombinant *T. pallidum* antigens (TpN15, TpN 17, TpN 47) are vortexed for 5 seconds at the highest setting. Thereafter, 5 µl of a patient serum as well as 25 µl of the particle reagent are pipetted into the reaction chamber. After 5 minutes of incubation at room temperature a magnet (LifeSep 1.5 S Magnetic Separation Unit, Dexter Magnetic Technologies, USA) is held to the base of the negative vessel. Result: Patient serums containing antibodies against one or more of the syphilis antigens on the particles, agglutinate the particles, so that they are retained in the capillary system similarly to the erythrocytes. Serums of non-infected persons do not agglutinate the particles. This causes the free particles to settle in the form of a visible brownish "button" in the lower region of the negative vessel.

7. Determination of Human Parvovirus B19 Antigen

5 µl of a PBS-buffer, titrated to pH 5.8, are pipetted into a reagent application channel of a carrier element. Thereafter 10 µl of a suspension of papainised test cells, carrying the blood group antigen P, are pipetted into the reaction chamber, whereupon 10 µl of a solution of recombinant VP2 particles are pipetted into this reaction chamber and the mixture is immediately centrifuged in the ID-centrifuge. Result: The cells are haemagglutinated, the haemagglutinates are retained in the capillary system. The negative vessel of this reactor remains cell-free. If, instead of the VP2 particles, the serum of a non viremic person is used, the erythrocytes collect visibly in the lower region of the negative vessel after centrifuging.

The invention claimed is:

1. A device for detecting one or more analytes in a sample, the device comprising:
   one or more reaction chambers adapted to receive the sample,
   optionally, one or more reagent application channels,
   one or more capillary systems connected to the reaction chambers or the reagent application channels, and
   one or more negative vessels connected to the capillary system or the capillary systems,
   wherein each of the capillary systems comprises capillary planes of diminishing cross-section which are disposed one below the other, and each capillary system comprises at least one capillary.

2. The device according to claim 1, wherein in each capillary plane a plurality of capillaries are arranged in an adjoining or bundled fashion.

3. The device according to claim 2, wherein adjoining or bundled capillaries of a capillary plane additionally comprise connecting webs.

4. The device according to claim 2, wherein adjoining or bundled capillaries of a capillary plane have the same inner cross-sectional area.

5. The device according to claim 1, wherein, the more distant the inner cross-sectional area of the capillary planes is disposed from the reaction chamber, the smaller it becomes.

6. The device according to claim 1, wherein the capillary planes of the capillary system are connected by chambers, whose inner cross-sectional area is preferably the same as that of the largest capillary.

7. The device according to claim 1, wherein the reagent application channel has 1.2 times the volume compared with the capillary or the capillary system plus the negative vessel.

8. The device according to claim 1, wherein the negative vessel has a larger volume than a volume of compacted sediment of the cells or particles used.

9. The device according to claim 1, wherein the negative vessel has a shape, which tapers towards the bottom.

10. The device according to claim 1, further comprising one or more ventilation channels.

11. The device according to claim 1, wherein the capillary system forms an integral component of the carrier element.

12. A method for detecting one or more analytes in a sample fluid by the visualization of agglutination, the method comprising the steps of:
 a) contacting the sample with a reagent to form a reaction mixture,
 b) exposing the reaction mixture to the effects of gravitation or magnetism, and passing the reaction mixture through the capillary system of the device according to claim 1, followed by a negative vessel of the device according to claim 1,
 and
 c) determining the reaction between the analyte and the reagent.

13. The method according to claim 12, wherein the reaction mixture is brought into contact with a further reagent during process step b).

14. The method according to claim 12, wherein the order of the individual process steps consisting of a) and b) are reversed, in particular when the sample fluid is brought into contact with a reagent only during the action of gravitation or magnetism.

15. The method according to any one of claims 12 to 14, wherein the sample fluid and/or the reagent include one or more particles.

16. The method according to any one of claims 12 to 14, wherein the reaction is determined optically.

17. The method according to claim 15, wherein the particles have a natural color or are colored.

18. The method according to claim 15, wherein the particles are color-, radio-, fluorescent- or enzyme-coded.

19. The method according to claim 15, wherein the particles include erythrocytes and/or thrombocytes and/or leucocytes or parts thereof.

20. The method according to claim 15, wherein the particles are pre-treated with proteolytic enzymes in order to enhance the reaction.

21. The method according to claim 15, wherein the reagent comprises antibodies selected from the group consisting of peptides, proteins, carbohydrates, lipids, nucleic acids, viruses, bacteria, parasites, human cells, animal cells plant cells, and parts thereof bound to the particles.

22. The method according to claim 15, wherein antigens or other ligands are bound to the particles.

23. The method according to claim 15, wherein the particles comprise polystyrene, polybromostyrene, gelatine, melamine, polymerised agarose or polymethyl methacrylate.

24. The method according to claim 15, wherein the particles are magnetic or paramagnetic.

25. The method according to any one of claims 12 to 14, wherein the sample mixture is exposed to gravitation by being subjected to centrifuging.

26. The method according to any one of claims 12 to 14, wherein the sample mixture is exposed to magnetism.

27. The method according to any one of claims 12 to 14, wherein the sample fluid comprises human, animal or plant material.

28. The method according to any one of claims 12 to 14, wherein the reagent comprises antibodies, test cells, synthetic particles, buffers or booster solutions.

29. The method according to any one of claims 12 to 14, wherein glycerin or other molecules are added to the reagent in order to increase the specific density of the solution.

30. The method according to any one of claim 12 to 14 wherein the analyte is at least one of: blood groups, antibodies against blood group characteristics, compatibilities between stored blood and recipients, thrombocyte characteristics and antibodies directed against thrombocytes, leucocyte characteristics and antibodies directed against leucocytes, haemagglutinating viruses, antibodies against proteins, viruses, bacteria, parasites, viral or bacterial or parasitic or other antigens, auto-antibodies, and antibodies directed against allergens.

31. The method according to claim 22 in which the other ligands are selected from the group consisting of peptides, proteins, carbohydrates, lipids, nucleic acids, viruses, bacteria, parasites, human cells, animal cells, plant cells, allergens, and parts thereof.

* * * * *